United States Patent [19]
McNaughton

[11] Patent Number: 4,874,383
[45] Date of Patent: Oct. 17, 1989

[54] SYRINGE SHIELD

[76] Inventor: R. David McNaughton, 95 Dobler Ave., Red Deer, Alberta, Canada, T4R 1X3

[21] Appl. No.: 130,277

[22] Filed: Dec. 8, 1987

[30] Foreign Application Priority Data

Mar. 17, 1987 [CA] Canada ................................. 532233

[51] Int. Cl.⁴ ............................................ A61M 5/32
[52] U.S. Cl. ..................................... 604/198; 604/263
[58] Field of Search ............... 604/198, 192, 197, 187, 604/263

[56] References Cited

U.S. PATENT DOCUMENTS

| 2,571,653 | 1/1951 | Bastien . |
| 2,845,065 | 6/1958 | Gabriel . |
| 3,073,306 | 9/1963 | Linder . |
| 3,783,998 | 8/1974 | Brush et al. . |
| 4,356,822 | 7/1982 | Winstead-Hall . |
| 4,425,120 | 3/1984 | Sampson et al. . |
| 4,573,976 | 2/1986 | Sampson et al. . |
| 4,631,057 | 11/1986 | Mitchell . |
| 4,666,435 | 5/1987 | Braginetz ............................ 604/198 |
| 4,702,738 | 10/1987 | Spencer ................................ 604/198 |
| 4,723,943 | 2/1988 | Spencer ......................... 604/263 X |
| 4,743,233 | 5/1988 | Schneider ........................... 604/192 |

FOREIGN PATENT DOCUMENTS

| 593228 | 2/1960 | Canada . |
| 689751 | 2/1964 | Canada . |
| 912389 | 4/1972 | Canada . |
| 953594 | 10/1974 | Canada . |
| 100102 | 5/1976 | Canada . |
| 1164753 | 4/1984 | Canada . |

Primary Examiner—John D. Yasko
Attorney, Agent, or Firm—Karen M. Gerken; Martin P. Hoffman; Mitchell B. Wasson

[57] ABSTRACT

Disclosed are hypodermic syringes having special safety features for preventing the user from inadvertently pricking himself with the needle. In the preferred embodiment the barrel of, for example, a syringe is provided with a sleeve that can be drawn out over the needle and firmly locked into position to prevent accidental contact of the user with the needle.

5 Claims, 2 Drawing Sheets

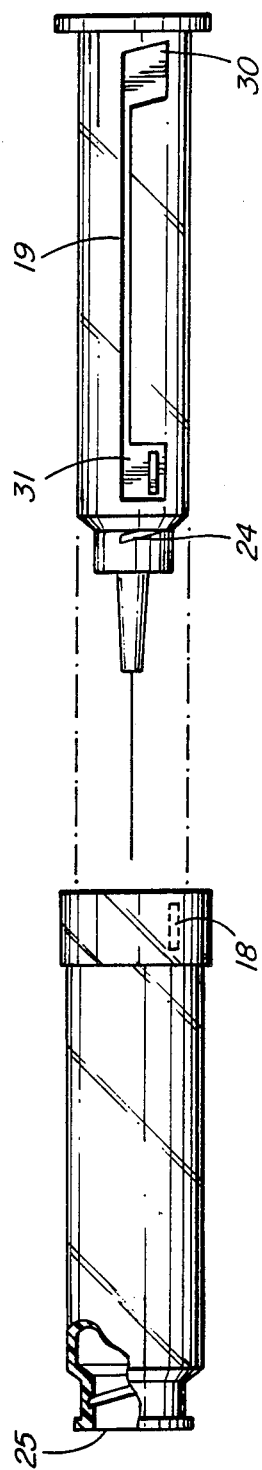
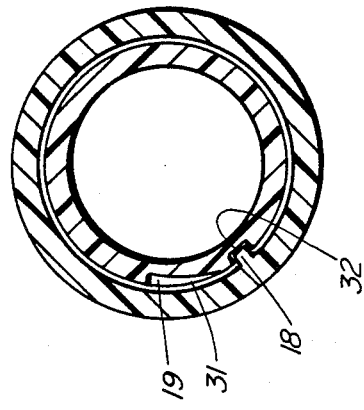
FIG. 3
FIG. 4

SYRINGE SHIELD

FIELD OF THE INVENTION

This invention relates to hypodermic needles, especially a syringe assembly, and specifically to such an assembly that is safe to use in a medical environment.

DESCRIPTION OF THE PRIOR ART

Typical means for ensuring the sterility of a hypodermic needle prior to use, and for the protection of a handler subsequent to use, include the familiar cap that seats on a collar surrounding the needle. However, these caps do not reliably protect persons handling the syringe after use. There have been numerous instances of injuries and consequent infection caused by users trying to slide a cap back over a needle, and in doing so puncturing their own skins. While in many instances little harm results from such injuries, with the advent of auto-immune disease syndrome (AIDS) medical persons have viewed with greater alarm the ease with which a potentially contaminated needle can puncture the skin of anyone handling the syringe subsequent to the administration of an injection to or the withdrawal of blood from a patient who may have a highly communicable disease.

The typical modern syringe is a disposable item having a plunger, barrel and needle with a protective cap over the needle. Many attempts have been made to improve on the conventional needle protection means described above, and perhaps the most relevant known to applicant is disclosed in U.S. Pat. No. 4 536 822 granted on Nov. 2, 1982 (Winstead-Hall). The syringe disclosed in the patent has the usual barrel, plunger and needle, however, an additional sleeve is slidable over the barrel. The primary purpose of the sleeve is to provide a means for determining precisely the depth of penetration of the needle 6, in FIG. 1 of the patent, into human tissue. The patentee clearly had in mind safety, i.e., minimizing undesired puncture wounds by the user, however, the patent does not address the problem of the security of the sleeve when it is positioned over the needle subsequent to the use of the syringe.

There remains a need for a disposable syringe assembly having a safety cover which, once locked in position, cannot, without the use of considerable force, be removed from its locked position.

SUMMARY OF THE INVENTION

The present invention overcomes the disadvantages of the prior art identified above by providing locking means between an auxiliary sleeve and the barrel of the syringe for securely locking the sleeve in a fully extended position in which the needle is fully covered to prevent injury to a user by the needle. Preferably, a screw-on cap is provided to place over the end of the sleeve once it has been fully extended and locked in position. The sleeve and barrel assembly has utility in other like transcutaneous articles, such as trocans, and the invention is not limited to syringes.

The invention provides a cheaply constructed, disposable syringe that materially improves safety in that a deliberate and almost self-destructive act would be required before the needle could contaminate the user.

BRIEF DESCRIPTION OF THE DRAWINGS

In the drawings, which illustrate an embodiments of the invention;

FIG. 3 is an illustration of the syringe with the sheath separated therefrom, and;

FIG. 4 is a section on the line 4—4 of FIG. 2.

Figure 1:
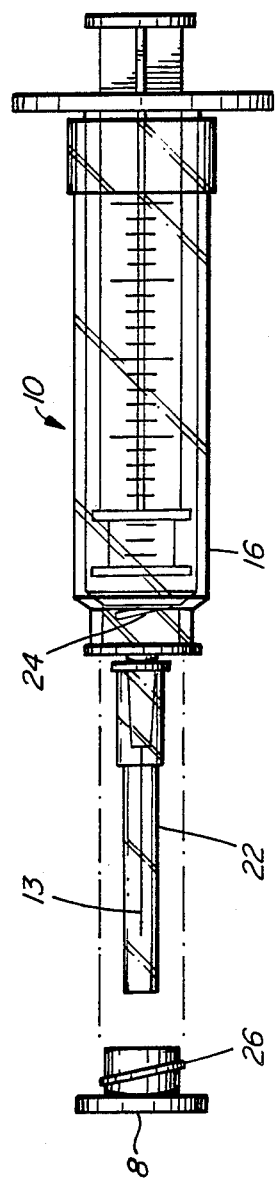
FIG. 1 is a side elevation of a syringe according to the invention.

In the drawings, 10 is a typical syringe having a barrel 11, a plunger 12 bearing a piston 15, and a needle 13. Indicia 14 on the barrel 11 indicate, by reference to the end of the piston 15, the amount of fluid drawn into the syringe, as is well known.

A sleeve 16 is dimensioned to fit closely over the barrel 11 so that in its initial position it covers the barrel 11 entirely, allowing the needle 13 to project beyond the end of the sleeve, that is, to the left in FIG. 1. The syringe is provided, as packaged, with a standard smaller sleeve 17 of the type known in the art which, in the case of the present invention, is removed prior to use and discarded, since it need not be used again. Barrel 11 and sleeve 16 are formed from a suitable plastic material.

Figure 2:
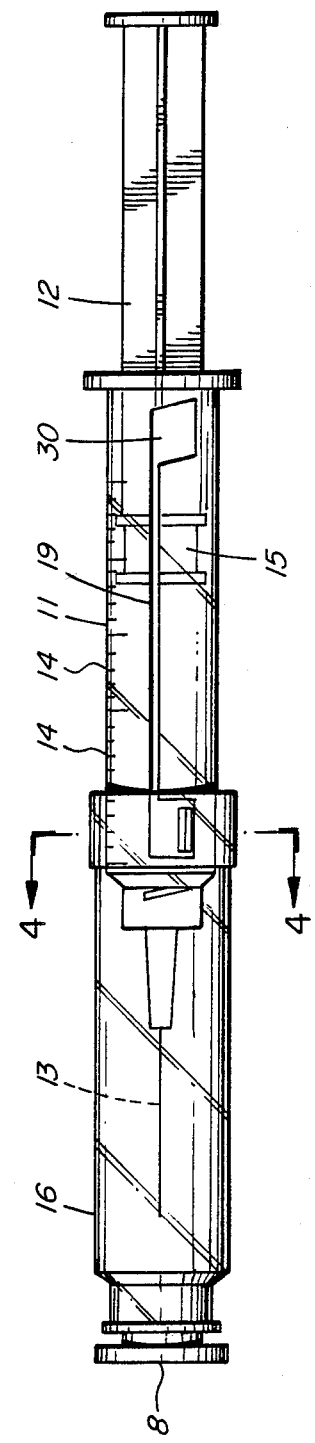
FIG. 2 is a view similar to FIG. 1 with its protective sheath extended.

The sleeve 16 is secured prior to use by the screw threads at 24 on the outside of the barrel 11, and matching screw threads 25 on the inside of the distal end of the sleeve. The screw threads 24 are formed, in a manner known in the art, such that a quarter-turn of the sleeve 16 in relation to the barrel 11 releases the sleeve 16 for axial movement along the barrel 11. In FIG. 2, the sleeve 16 is shown fully extended to a position where it entirely covers the needle 13, and it is impossible to make accidental physical contact with the needle. Preferably, a cap 8 is provided having external threads 26 matching the threads 25. The cap is packaged with the syringe 10 and used to ensure the safety of the assembly after use.

Illustrated on the outside of the barrel 11 is a formation, in the plastic material from which the barrel is formed, of a feature critical to the invention, i.e., the aforementioned secure locking means. Formed on the inside of the sleeve 16 is a protrusion 18 that extends radially inwardly a short distance corresponding to a groove 19 (FIG. 2) formed in the outside of the barrel 11. The groove 19 extends axially along the barrel, and its right hand or inner end extends circumferentially to permit the aforementioned quarter turn locking of the sleeve in the rest position via the threads 24,25. The radial extension 30 of the groove 19 therefore extends over a quarter, or slightly more than a quarter, of the circumference of the barrel 11. At the opposite or outer end of the groove 11, a ramp 31 is formed extending in depth from its mosumium at the groove 19 radially outwardly to a recess 32 corresponding in size and shape to the protrusion 18. Thus, once the sleeve has been rotated a quarter turn freeing it from the threads 24 and freeing it from the portion 30 of the groove, the sleeve can be pulled along the barrel with the protrusion 18 engaged in the groove 19 to its outermost or left hand position. Rotation of the sleeve 16 then causes the protrusion 18 to ride resiliently up the ramp 31 and drop into the recess 32, thus locking the sleeve firmly in the disposal position shown in FIG. 2. It will be appreciated that the sleeve 16 cannot be removed from the locked position without considerable force applied either torsionally or axially and as a consequence the user is protected, as are, for example, cleaning staff. The cap 8 is subsequently screwed into position in the barrel to complete the protective covering.

It will also be understood that while the invention is primarily intended for use with a syringe, other assemblies having percutaneous needles can be equipped in like manner with protective sleeves.

What I claim is:

1. A syringe comprising:
   a barrel having a hypodermic needle mounted on one end thereof, said barrel being of transparent cylindrical form over the major portion of its length;
   a piston mounted for movement longitudinally within said barrel and connected to a handle that projects from the opposite end of said barrel;
   a sleeve dimensioned to fit over said barrel, and mounted to be slidable therealong, said sleeve having an internal projection and being movable axially between an extended position wherein it projects from said one end of said barrel beyond the tip of said needle and a retracted position wherein it coaxially surrounds said barrel and exposes said needle for use, said sleeves having a length that corresponds to that of said barrel and comprising a cylindrical wall that is transparent such that in said retracted position it affords unimpeded visibility of substantially the entire extent of said transparent portion and thus the interior of said barrel;
   first locking means for securely locking said sleeve in said extended position in which said needle is fully covered to prevent injury to a user by said needle, said first locking means comprising walls that define a locking recess in said barrel into which recess said internal projection can be positioned by predetermined movement of said sleeve relative to said barrel in said extended position, said barrel including an inclined ramp that approaches said locking recess to guide and facilitate entry of said projection into said recess; and
   a second locking means to securely lock said sleeve when in said retracted position against axial movement relative to said barrel.

2. A syringe comprising:
   a barrel having a hypodermic needle mounted on one end thereof, said barrel being of transparent cylindrical form over the major portion of its length;
   a piston mounted for movement longitudinally within said barrel and connected to a handle that projects from the opposite end of said barrel;
   a sleeve dimensioned to fit over said barrel, and mounted to be slidable therealong, said sleeve being movable axially between an extended position wherein it projects from said one end of said barrel beyond the tip of said needle and a retracted position wherein it coaxially surrounds said barrel and exposes said needle for use, said sleeve having a length that corresponds to that of said barrel and comprising a cylindrical wall that is transparent such that in said retracted position it affords unimpeded visibility of substantially the entire extent of said transparent portion and thus the interior of said barrel;
   a projection on the inside of said sleeve, a mating groove extending along the outside of said barrel, the ends of said groove being adjacent the ends of said barrel, an inclined ramp extending from said groove and terminating in a recess that comprises first locking means for securely locking said sleeve in said extended position in which said needle is fully covered to prevent injury to a user by said needle, said recess being dimensioned to accommodate and retain said projection, said projection being movable along said groove as said sleeve is moved along said barrel until said projection registers with said ramp, further movement of said sleeve causing said projection to move up said ramp and then to drop into said recess to lock said sleeve in the extended position; and
   second locking means to securely lock said sleeve when in said retracted position against axial movement relative to said barrel.

3. A syringe as claimed in claim 2 wherein said second locking means comprises a screw-thread formed on an end portion of said sleeve and engageable with a mating screw-thread formed on said barrel when said sleeve is in the retracted position to lock said sleeve against axial movement, said groove having a circumferential extension to accommodate said projection during rotation of said sleeve upon engagement or disengagement of said mating screw threads.

4. A syringe as claimed in claim 3 wherein the rotation of said sleeve to effect full engagement of said screw-threads amounts to approximately one quarter of a full rotation.

5. A syringe as claimed in claim 4 further comprising a screw-threaded cap engageable with said screw-thread on said sleeve when the latter is in the extended condition to completely close the associated end of the sleeve.

* * * * *